United States Patent
Baldauf

(10) Patent No.: US 7,527,848 B2
(45) Date of Patent: *May 5, 2009

(54) LAMINATE MATERIAL FOR HOOK-AND-LOOP CLOSURES

(75) Inventor: Georg Baldauf, Laer (DE)

(73) Assignee: Nordenia Deutschland Gronau GmbH, Gronau (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/960,231

(22) Filed: Oct. 7, 2004

(65) Prior Publication Data

US 2005/0208260 A1    Sep. 22, 2005

(30) Foreign Application Priority Data

Mar. 22, 2004 (EP) ................... 04006783

(51) Int. Cl.
- B32B 3/00 (2006.01)
- B32B 3/06 (2006.01)
- B32B 27/14 (2006.01)

(52) U.S. Cl. ................ 428/99; 428/98; 428/100; 428/198; 428/197; 428/196

(58) Field of Classification Search ............ 428/99, 428/100, 95, 195, 198, 197, 195.1, 196
See application file for complete search history.

(56) References Cited

U.S. PATENT DOCUMENTS

| | | | |
|---|---|---|---|
| 4,159,360 A * | 6/1979 | Kim ................ | 428/195.1 |
| 5,032,122 A | 7/1991 | Noel et al. | |
| 5,318,555 A | 6/1994 | Siebers et al. | |
| 5,326,612 A | 7/1994 | Goulait | |
| 5,614,281 A * | 3/1997 | Jackson et al. ........ | 428/100 |
| 5,616,394 A * | 4/1997 | Gorman et al. ........ | 428/99 |
| 5,736,214 A | 4/1998 | Billarant | |
| 5,763,041 A * | 6/1998 | Leak et al. ........... | 428/100 |
| 5,858,515 A * | 1/1999 | Stokes et al. ......... | 428/195.1 |
| 5,876,532 A | 3/1999 | Billarant | |
| 5,888,607 A * | 3/1999 | Seth et al. ........... | 428/92 |
| 5,904,793 A | 5/1999 | Gorman et al. | |
| 5,997,981 A * | 12/1999 | McCormack et al. .... | 428/99 |

(Continued)

FOREIGN PATENT DOCUMENTS

EP    0 777 006    6/1997

(Continued)

Primary Examiner—Cheryl Juska
(74) Attorney, Agent, or Firm—Collard & Roe, P.C.

(57) ABSTRACT

A laminate material for hook-and-loop closures, comprising a carrier film and a textile substrate laminated onto the carrier film. The textile substrate has loops on its surface that are suitable for connecting with hook-and-loop hooks, wherein the carrier film and the textile substrate are not connected over their entire area. A method for producing a laminate material for hook-and-loop closures comprises applying an adhesive to a carrier film in a pattern that is composed of adhesive areas and adhesive-free regions, applying a material web of a textile substrate to the side of the carrier film provided with adhesive to form a two-ply web, the textile substrate having loops on its surface that are suitable for connecting with hook-and-loop hooks; and passing the two-ply web through a roller nip of a pair of rollers, which presses the carrier film and the textile substrate together.

5 Claims, 5 Drawing Sheets

U.S. PATENT DOCUMENTS

| | | | | |
|---|---|---|---|---|
| 6,150,002 | A * | 11/2000 | Varona | 428/99 |
| 6,197,404 | B1 * | 3/2001 | Varona | 428/152 |
| 6,238,767 | B1 * | 5/2001 | McCormack et al. | 428/99 |
| 6,316,687 | B1 * | 11/2001 | Davis et al. | 604/372 |
| 6,589,638 | B1 * | 7/2003 | McCormack et al. | 428/198 |
| 6,770,065 | B1 * | 8/2004 | Sasaki et al. | 604/391 |
| 6,910,353 | B2 * | 6/2005 | Sasser et al. | 66/191 |
| 7,160,600 | B2 * | 1/2007 | Shepard et al. | 428/99 |
| 7,422,991 | B2 * | 9/2008 | Baldauf et al. | 442/381 |
| 7,470,340 | B2 * | 12/2008 | Baldauf et al. | 156/73.1 |
| 2002/0006758 | A1 * | 1/2002 | Desgrand | 442/312 |
| 2005/0130543 | A1 * | 6/2005 | Baldauf | 442/394 |
| 2006/0019572 | A1 * | 1/2006 | Lester et al. | 442/411 |
| 2006/0080810 | A1 * | 4/2006 | Horn et al. | 24/445 |
| 2006/0162843 | A1 * | 7/2006 | Baldauf et al. | 156/73.1 |
| 2006/0180272 | A1 * | 8/2006 | Baldauf | 156/290 |
| 2006/0182927 | A1 * | 8/2006 | Baldauf | 428/99 |
| 2006/0247567 | A1 * | 11/2006 | Baldauf et al. | 604/1 |
| 2006/0292328 | A1 * | 12/2006 | Baldauf et al. | 428/77 |

FOREIGN PATENT DOCUMENTS

JP  2004236960 A * 8/2004

* cited by examiner

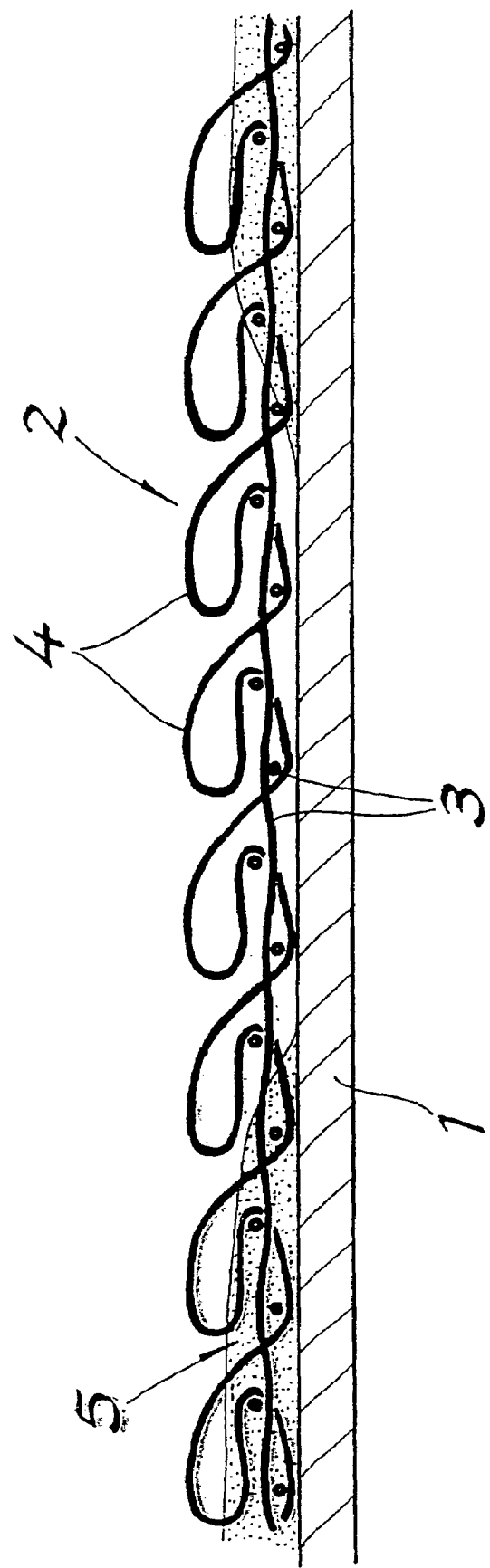

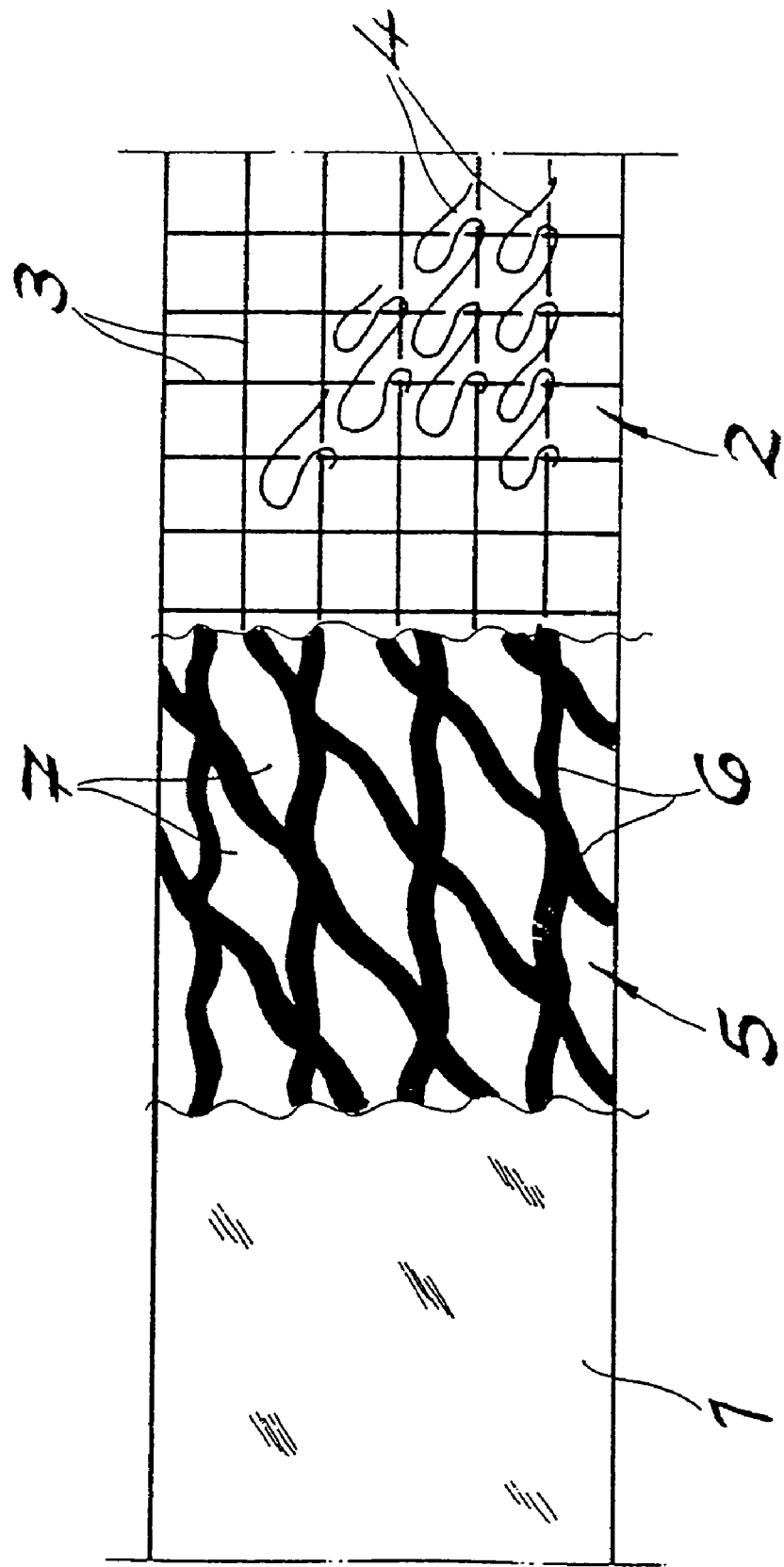

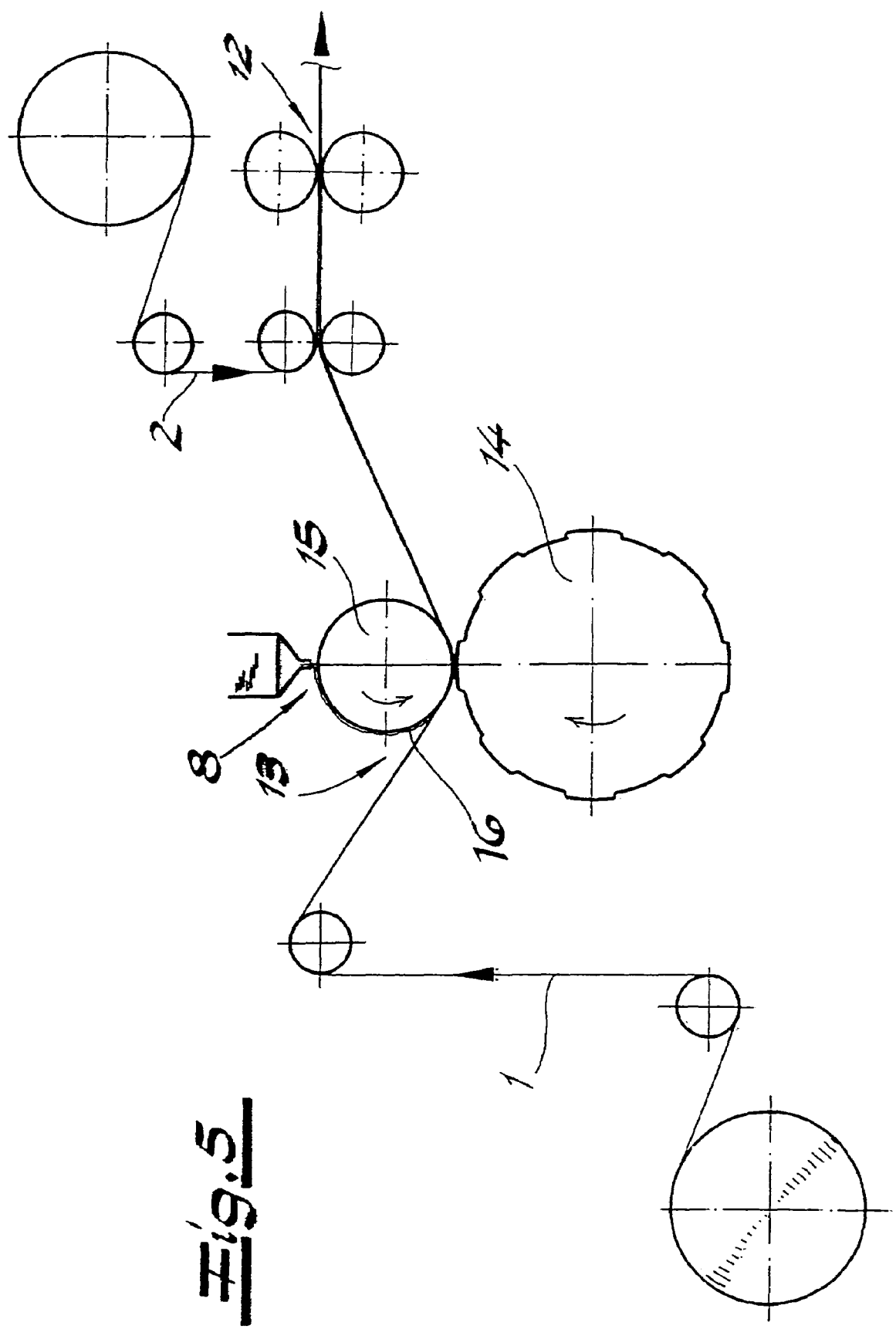

LAMINATE MATERIAL FOR HOOK-AND-LOOP CLOSURES

BACKGROUND OF THE INVENTION

1. Field of the Invention

The invention relates to a laminate material for hook-and-loop closures, particularly diaper closures, having a carrier film and a textile substrate laminated onto the carrier film. The textile substrate has loops on the surface, suitable for connecting with hook-and-loop hooks.

2. The Prior Art

The laminate material forms the female part of a hook-and-loop closure. When used for diapers, strips of the laminate material are affixed to the front waistband region of the diapers. The hook-and-loop loop closure is made complete with closure bands that are attached to the diapers on the side, and have hook-and-loop hooks on their free end. Hook-and-loop closures can be opened and closed multiple times without any detrimental effect on their functionality. In contrast to adhesive closures, hook-and-loop closures are not sensitive to contact with skin creams or powder.

Several requirements are set for a laminate material for hook-and-loop closures on disposable products, e.g. baby diapers. The textile substrate should have as low a weight per unit area as possible, so that it can be produced inexpensively. It should be translucent, so that the surface of the carrier film, which is usually imprinted, is visible. Furthermore, the textile substrate must guarantee sufficient hook engagement with the hook-and-loop hooks or the related closure band, despite a low weight per unit area. A sufficient number of freely movable hooks is required, the function of which is not allowed to be impaired by the adhesive connection between the carrier film and the textile substrate. In order to guarantee a functionally reliable adhesive connection between the textile substrate and the carrier film, a sufficiently thick adhesive film must be applied. When the textile substrate and the carrier film are pressed onto one another in a laminating unit, by means of a pair of rollers, the fibers of the textile substrate sink into the adhesive film, and are surrounded by the adhesive film. After the adhesive film has cured, the yarns of the textile are securely anchored on the carrier film, but large amounts of adhesive bring with them the risk that the loops that are required for the function of the hook closure are also glued down, and thereby lose their ability to function. This becomes evident in an insufficient hook-and-loop effect.

A laminate material for hook-and-loop closures, having the characteristics described initially, is shown in European Patent No. EP 0 777 006 B1. The textile substrate consists of an interlaid scrim of warp and weft threads, and loops that are connected with the interlaid scrim by means of knitting technology. The textile substrate is glued to the carrier film. The loops are dimensioned to be so large that they rest on the mesh formed by the basic interlaid scrim. The result is that the loops do not come into contact with the adhesive, and retain their ability to function. However, the problem explained above, of assuring both a good hook-and-loop effect and a high laminate strength between the carrier film and the substrate, when using an open textile substrate, is not solved to its full extent. The connection between the carrier film and the textile substrate, in particular, is still in need of improvement.

SUMMARY OF THE INVENTION

It is therefore an object of the invention to configure the connection between the carrier film and the textile substrate of a laminate material for hook-and-loop closures in such a manner that an improved hook-and-loop effect as compared with the state of the art is obtained, at a high laminate strength.

This task is accomplished in that the carrier film and the textile substrate are not connected over their entire area. The area on which the carrier film is connected with the textile substrate preferably amounts to 20 to 80% of the laminated film area. According to the invention, the carrier film and the textile substrate rest loosely on one another on part of the laminated area. In these regions, in which the carrier film and the textile substrate are not connected with one another, the hook-and-loop hooks can hook under the textile material well, since they can submerge deeply into the textile substrate. Another contributing factor for a good connection is that not only are the surface loops available to the hook-and-loop hooks, but also, the hook-and-loop hooks can also hook into the basic interlaid scrim of the textile substrate.

In a further embodiment, the carrier film and the textile substrate are glued to one another, whereby the adhesive is applied in a pattern that is composed of adhesive areas and adhesive-free regions. The teaching according to the invention allows very high laminate adhesion values between the textile substrate and the carrier film, with a simultaneous good hook-and-loop effect. A large amount of adhesive can be selected in the region of the adhesive areas, which assures a reliable, non-positive lock connection between the textile substrate and the carrier film, whereby an extensive saturation of the textile material at the adhesive areas can also be acceptable. The adhesive-free regions, adjacent to the adhesive areas, remain fully maintained for the connection with the hook-and-loop hooks. The hook-and-loop hooks can be pushed deeply into the textile substrate in the adhesive-free regions, in which the carrier film and the textile substrate rest loosely on one another.

In addition to the loops on the surface, the yarns that form the basic interlaid scrim of the textile substrate are also available for anchoring the hook-and-loop hooks, in the adhesive-free regions. The hook-and-loop hooks can engage behind the yarns of the basic interlaid scrim. In this way, the laminate material is given a hook-and-loop effect that is significantly greater than in the case of a full-area glue connection between the textile substrate and the carrier film.

Essentially, the available connection area of the laminated material is divided up into adhesive areas that exclusively or at least primarily produce a reliable connection between the carrier film and the textile substrate, and adhesive-free regions, in which a good hook-and-loop effect between the textile substrate and the hook-and-loop hooks is guaranteed. Adhesive-free regions and adhesive areas alternate in such a manner that strips for hook-and-loop closures, having good usage properties, can be cut out of the laminate material.

Varied adhesive patterns for connecting the carrier film and the textile substrate can be used within the scope of the teaching according to the invention. A point-by-point glue connection between the carrier film and the textile substrate lies within the scope of the invention. Furthermore, there is the possibility that the adhesive forms a pattern of parallel or intersecting strips, whereby the strips can be configured as straight lines or wave-shaped lines. Another preferred embodiment of the invention provides that the adhesive forms a pattern having a cell-shaped structure, whereby the cell-shaped structure has open cells with adhesive-free regions, or closed cells with adhesive areas. Cell structures having open cells free of adhesive prove to be particularly effective.

According to a preferred embodiment of the invention, the textile substrate consists of a warp-knitted fabric that has a basic interlaid scrim made of filament yarns, and loops connected with the interlaid scrim by means of knitting technology. It is practical if the warp-knitted fabric has a weight per unit area of between 5 g/m² and 50 g/m². It is translucent and very air-permeable.

The invention allows the processing of textile substrates having a low weight per unit area to produce functional diaper closures. The textile substrate can consist of monofilament and/or multifilament yarns, for example of polypropylene, polyester, polyamide, or other synthetics that can be processed by means of textile technology.

According to a preferred embodiment, the carrier film also has a weight per unit area between 5 g/m² and 50 g/m². Mono-films as well as multi-layer co-extruded or laminated films can be used. Suitable films are, for example, films made of polyethylene, polypropylene, polyester, polyamide, as well as mixtures and co-polymerizates based on these polymers. Preferably, carrier films are used, the surface of which can be imprinted using sheet printing. Imprinted and/or embossed carrier films can be used.

Fundamentally, any adhesives used in the field of laminated films can be used to glue the textile substrate and the carrier film together. Hot-melt glues on the basis of PAO, EVA, SBS, SIS, reactive polyurethane adhesives, acrylate adhesives, as well as radiation-cured adhesives are preferred.

A method for the production of the laminate material described above, is also an object of the invention.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 1 shows a longitudinal section through a laminate material for hook-and-loop closures;

FIG. 2 shows a top view of the laminate material shown in FIG. 1, and its layers;

FIGS. 4 and 5 show a device for producing the laminate material in different embodiments.

DETAILED DESCRIPTION OF THE PREFERRED EMBODIMENT

Figure 3A:
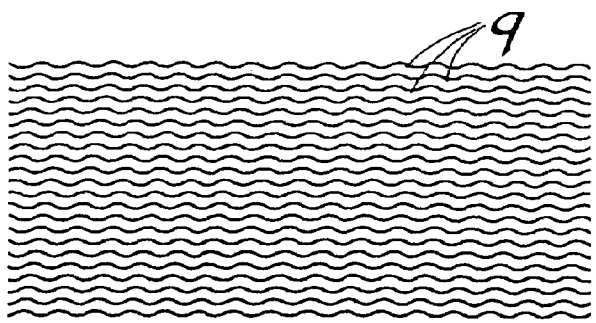
FIGS. 3a to 3e show adhesive patterns that form a connecting layer between the carrier film and the textile substrate of the laminate material shown in FIGS. 1 and 2.

Referring now in detail to the drawings, the laminate-material shown schematically in FIGS. 1 and 2 can be used as the female part of hook-and-loop closures. The laminate material is particularly intended for hook-and-loop closures on disposable products, for example baby diapers. It consists of a carrier film 1 and a textile substrate 2 laminated onto carrier film 1. The substrate, as a warp-knitted fabric, has a basic interlaid scrim 3 made of filament yarns, as well as loops 4 that are connected with basic interlaid scrim 3 by means of knitting technology. Loops 4 are arranged on the surface and are suitable for connecting with hook-and-loop hooks, not shown, of a closure band.

Carrier film 1 and textile substrate 2 are not connected over their entire area. The area on which carrier film 1 is connected with textile substrate 2 preferably amounts to 20 to 80% of the laminated film area.

From the representations in FIGS. 1 and 2, carrier film 1 and the textile substrate 2 are glued to one another, whereby the adhesive that forms connecting layer 5 is applied in a pattern that is composed of adhesive areas 6 and adhesive-free regions 7. In adhesive areas 6, textile substrate 2 is firmly anchored to carrier film 1 by means of an application 8 of adhesive, which can be variably determined. From FIG. 1, it is evident that the filaments of textile substrate 2 have sunk into the adhesive, for example a hot-melt glue, and are surrounded by it. In this connection, it can be acceptable that loops in the region of adhesive areas 6 are also partly glued down, and have only little effect in the region of the adhesive areas 6. In adhesive-free regions 7, the carrier film 1 and textile substrate 2 lie loosely on one another. In adhesive-free regions 7 of the laminate material, the hook-and-loop hooks can be pushed deeply into textile substrate 2 and hooked into free loops 4 on the surface. In addition, the filament yarns of basic interlaid scrim 3 are also available for anchoring the hook-and-loop hooks. The hook-and-loop hooks engage behind the filament yarns of the textile substrate 2. Adhesive-free regions 7 of the laminate material are characterized by a good hook-and-loop effect, and give the laminate material good usage properties.

Figure 3B:
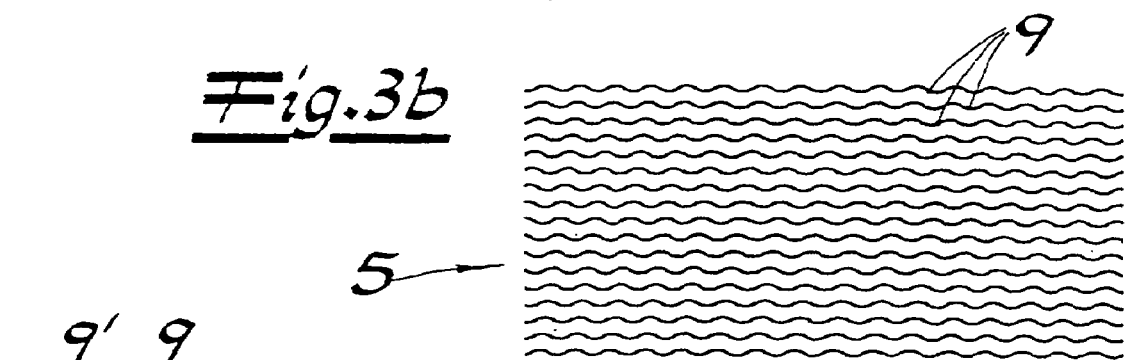
Figure 3C:
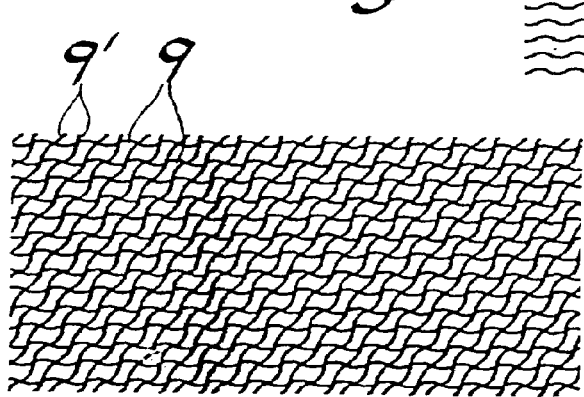
Figure 3D:
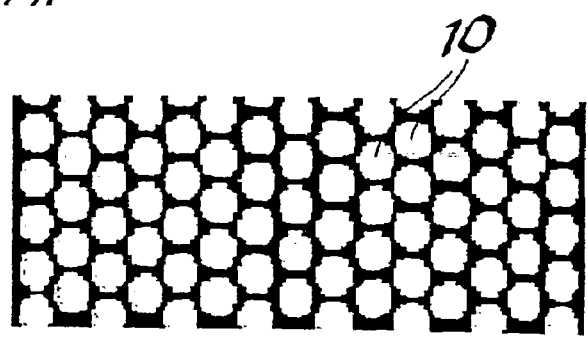
Figure 3E:
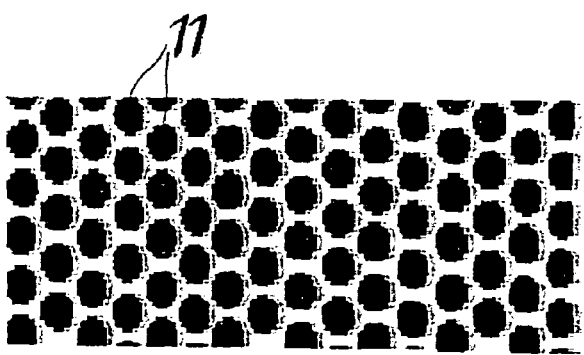

FIGS. 3a to 3e show different adhesive patterns of the connecting layer 5 between the carrier film and the textile substrate. In the exemplary embodiments 3a to 3b, the adhesive forms a pattern of parallel, wave-shaped strips 9. The patterns shown in FIGS. 3a and 3b differ from one another in the distance between adhesive strips 9 relative to one another. In the exemplary embodiment of FIG. 3c, the adhesive forms a pattern of intersecting strips 9, 9'. FIG. 3d shows an adhesive pattern having a cell-shaped structure, whereby the cell-shaped structure has open cells 10 having adhesive-free regions. In the exemplary embodiment shown in FIG. 3e, the adhesive also forms a pattern having a cell-shaped structure, whereby the cell-shaped structure, however, has closed cells 11 having adhesive areas. This results in point-by-point adhesion between carrier film 1 and textile substrate 2, whereby the number of adhesive points per unit area can be established by means of a few experiments. In all the exemplary embodiments, the adhesive areas are supposed to amount to not less than 20% and a maximum of 80% of the laminated area.

The textile substrate preferably has a weight per unit area between 5 g/m² and 50 g/m². It is air-permeable and translucent. The carrier film can be imprinted, because of the translucence of the textile substrate. Films made of polyolefins, polyester, polyamide, mixtures or co-polymerizates of these polymers, for example, can be used as carrier films. They preferably also have a weight per unit area between 5 g/m² and 50 g/m².

To glue the carrier film together with the textile substrate, hot-melt glues on the basis of PAO, EVA, SBS, SIS, reactive polyurethane adhesives, acrylate adhesives, as well as radiation-cured adhesive can be used. The amounts of adhesive are coordinated with the adhesive areas, in such a manner that a firm lamination between the carrier film and the textile substrate is formed. Therefore the amounts of applied adhesive can be established variably, depending on the use.

Figure 4:
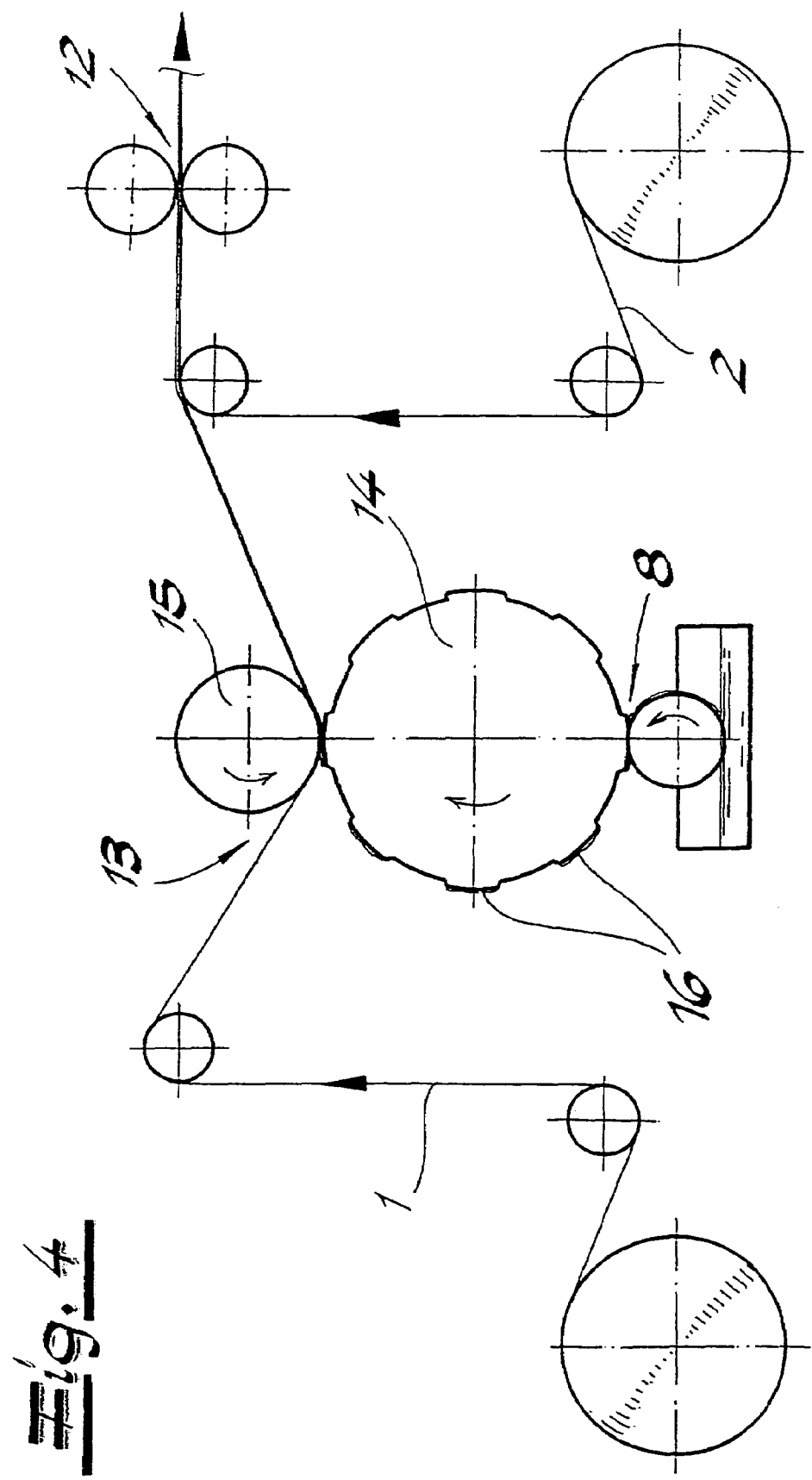

The method for the production of the laminate material is shown schematically in FIG. 4. Adhesive is applied to a carrier film 1 in a pattern that is composed of adhesive areas and adhesive-free regions. A material web made of a textile substrate 2, which has loops on the surface, suitable for connecting with hook-and-loop hooks, is applied to the side of carrier film 1 that is provided with adhesive. The two-ply web that is formed as a result passes through the roller nip of a pair of rollers 12, in which the carrier film 1 is pressed together with the textile substrate 2.

The adhesive can be applied to the carrier film by means of nozzle application methods, via spray technology, and similar methods. In the preferred embodiment of the method, the adhesive is applied to carrier film 1 by means of a rotation printing method. In this connection, carrier film 1 runs through a printing roller arrangement 13 consisting of an engraved cylinder 14 and a counter-cylinder that presses the film onto the engraved cylinder, whereby the surface of the engraved cylinder 14 is provided with an engraving that corresponds to the adhesive pattern. In the case of the embodiment of the method shown in FIG. 4, an adhesive film 16 is applied to the surface of engraved cylinder 14, which is transferred to carrier film 1 at the raised areas of the engraving. In the method variant shown in FIG. 5, adhesive film 16 is applied to the surface of counter-cylinder 15. However, the engraved cylinder 14 presses carrier film 1 against adhesive film 16 on the surface of counter-cylinder 15 exclusively in the raised regions of the engraving, so that the adhesive film is transferred to the carrier film only at the raised areas of the engraving.

EXAMPLES

The properties that are decisive for the functionality of a hook-and-loop closure are characterized by three measurement variables. The decisive measurement variables are opening force, shear force, as well as laminate adhesion between the textile substrate and the carrier film. Opening force is understood to mean the force that must be applied in order to loosen the hook-and-loop hooks of a hook-and-loop closure from the textile substrate. The opening force is determined by means of a tensile test, whereby the manual opening procedure is simulated by means of a tensile force measurement on the hook-and-loop closure, in the opening direction. The force at which the connection between the hook-and-loop hook and the textile substrate is loosened unintentionally, because of an overly great stress, is referred to as the maximal shear force. This force, too, is measured by means of a tensile force measurement, with simulation of the tensile stress that occurs during handling. The laminate adhesion between the textile substrate and the carrier film is determined in a peel test, by means of pulling the textile substrate off the carrier film.

Laminate materials were produced in accordance with the methods shown in FIGS. 4 and 5. The textile substrate and the carrier film were not changed. The amount of adhesive applied and the adhesive pattern for connecting the carrier film and the textile substrate were varied. Adhesive patterns in accordance with FIGS. 3a to 3c were selected, and in a comparison test, the carrier film was glued to the textile substrate over the entire area. The weight per unit area of the laminate material, which is slightly dependent on the amount of adhesive applied, the laminate adhesion, the opening force, and the shear force were measured. The measurements were carried out using samples having a hook-and-loop area of 25.4 mm length and 13 mm width. The test results are shown in Table 1. The laminate materials produced according to the method according to the invention are characterized by high laminate adhesion as well as good values for opening force and shear force.

Accordingly, while only a few embodiments of the present invention have been shown and described, it is obvious that many changes and modifications may be made thereunto without departing from the spirit and scope of the invention.

TABLE 1

| Adhesive pattern | Weight per unit area [g/m$^2$] | | |
|---|---|---|---|
| | A | B | C |
| Method according to FIG. 5 | 44.3 | 45.2 | 44.7 |
| Method according to FIG. 4 | 44.9 | 46.6 | 46.3 |
| Comparison test | | 46.0 | |

| Adhesive pattern | Laminate adhesion [N] | | | Opening force [N] | | | max. shear force [N] | | |
|---|---|---|---|---|---|---|---|---|---|
| | A | B | C | A | B | C | A | B | C |
| Method according to FIG. 5 | 12.1 | 10.8 | 10.5 | 4.0 | 3.2 | 4.7 | 40 | 37 | 41 |
| Method according to FIG. 4 | 7.3 | 11.7 | 9.2 | 5.5 | 6.4 | 7.5 | 44 | 43 | 50 |
| Comparison test | | 6.0 | | | 4.0 | | | 40 | |

A: adhesive pattern corresponding to FIG. 3a
B: adhesive pattern corresponding to FIG. 3c
C: adhesive pattern corresponding to FIG. 3b

What is claimed is:

1. A laminate material for hook-and-loop closures, comprising;
   a carrier film; and
   a textile substrate laminated onto the carrier film, said textile substrate being a warp-knitted fabric having a basic interlaid scrim of filament yarns and loops on a surface thereof that are connected with the basic interlaid scrim by means of knitting technology and are suitable for connecting with hook-and-loop hooks,
   wherein the carrier film and the textile substrate are glued to one another via adhesive applied to the carrier film in a pattern that is composed of adhesive areas and adhesive-free regions, wherein said adhesive pattern forms a cell-shaped pattern of open cells having adhesive-free regions, and wherein said cell-shaped adhesive pattern does not correspond to a construction pattern of the basic interlaid scrim,
   wherein in the region of adhesive areas the filament yarns forming the basic interlaid scrim are sunk into and surrounded by the adhesive areas and the loops are also partly glued down, and
   wherein the carrier film and the textile substrate lie loosely on one another in the adhesive free regions such that not only are the surface loops available to hook-and-loop hooks but also the hook-and-loop hooks can hook into the basic interlaid scrim of the textile substrate.

2. The laminate material according to claim 1, wherein the carrier film is connected with the textile substrate over an area comprising 20% to 80% of a total carrier film area.

3. The laminate material according to claim 1, wherein the textile substrate has a weight per unit area of 5 g/m$^2$ to 50 g/m$^2$.

4. The laminate material according to claim 1, wherein the carrier film is imprinted and/or embossed.

5. The laminate material according to claim 1, wherein the carrier film has a weight per unit area of 5 g/m$^2$ to 50 g/m$^2$.

* * * * *